United States Patent [19]

Breiphol et al.

[11] Patent Number: 5,565,606

[45] Date of Patent: Oct. 15, 1996

[54] SYNTHESIS OF PEPTIDE AMINOALKYLAMIDES AND PEPTIDE HYDRAZIDES BY THE SOLID-PHASE METHOD

[75] Inventors: Gerhard Breiphol; Jochen Knolle, both of Frankfurt am Main, Germany

[73] Assignee: Hoechst Aktiengesellschaft, Frankfurt am Main, Germany

[21] Appl. No.: 257,446

[22] Filed: Jun. 8, 1994

Related U.S. Application Data

[63] Continuation of Ser. No. 783,335, Oct. 28, 1991, abandoned, which is a continuation-in-part of Ser. No. 109,532, Oct. 19, 1987, abandoned, and a continuation-in-part of Ser. No. 218,798, Jul. 14, 1988, abandoned, and a continuation-in-part of Ser. No. 747,492, Aug. 19, 1991, abandoned, which is a continuation of Ser. No. 284,874, Dec. 14, 1988, abandoned.

[30] Foreign Application Priority Data

Oct. 21, 1986 [DE] Germany ........................... 36 35 670.0
Jul. 16, 1987 [DE] Germany ........................... 37 23 551.6
Dec. 11, 1987 [DE] Germany ........................... 37 42 633.8

[51] Int. Cl.$^6$ .................................................. C07C 261/00
[52] U.S. Cl. ........................ 560/158; 530/326; 546/335; 560/23; 560/26; 560/32; 560/55; 560/61; 560/66; 560/159
[58] Field of Search ........................... 560/159, 61, 66, 560/55, 32, 158; 543/335

[56] References Cited

U.S. PATENT DOCUMENTS

| | | | |
|---|---|---|---|
| 3,243,389 | 3/1966 | Moller | 560/159 |
| 3,287,398 | 11/1966 | Allais | 560/159 |
| 3,734,948 | 5/1973 | Sidi | 560/66 |
| 4,622,312 | 11/1986 | Felix et al. | 514/12 |
| 4,623,715 | 11/1986 | Geiger | 530/330 |
| 4,626,523 | 12/1986 | Vale, Jr. et al. | 514/12 |
| 4,643,989 | 2/1987 | Baird | 514/12 |
| 4,659,693 | 4/1987 | Nestor | 514/12 |
| 4,721,704 | 1/1988 | Chang et al. | 514/11 |
| 4,784,987 | 11/1988 | River et al. | 530/324 |
| 4,843,064 | 6/1989 | Vaughan et al. | 514/12 |

FOREIGN PATENT DOCUMENTS

| | | |
|---|---|---|
| 199018 | 10/1984 | European Pat. Off. . |
| 136475 | 4/1985 | European Pat. Off. . |
| 142487 | 5/1985 | European Pat. Off. . |
| 152333 | 8/1985 | European Pat. Off. . |
| 161852 | 11/1985 | European Pat. Off. . |
| 173557 | 3/1986 | European Pat. Off. . |
| 118214 | 7/1986 | European Pat. Off. . |
| 188214 | 7/1986 | European Pat. Off. . |
| 122818 | 10/1986 | European Pat. Off. . |
| 216517 | 4/1987 | European Pat. Off. . |
| 231752 | 8/1987 | European Pat. Off. . |
| 232078 | 8/1987 | European Pat. Off. . |
| 239558 | 9/1987 | European Pat. Off. . |
| 244169 | 11/1987 | European Pat. Off. . |
| 269220 | 6/1988 | European Pat. Off. . |
| 271041 | 6/1988 | European Pat. Off. . |
| 274916 | 7/1988 | European Pat. Off. . |
| 291999 | 11/1988 | European Pat. Off. . |
| 87/0272 | 8/1987 | South Africa . |
| 85/04870 | 11/1985 | WIPO . |

OTHER PUBLICATIONS

Atherton et al., The Solid Phase in Solid–Phase Synthesis, Perspective Chemistry, pp. 101–117, (1981).
Hubbuch Article, Schutsgruppen in der Peptidsynthese (Teil 1) Kontake (Merck) Mar. 1979, No. 3, pp. 14–23.
Schutzgruppentaktik, Amino— und Carboxyl–Schutzgruppen, English Translation of passage of original article from p. 16, line 20 through p. 19, line 3. (1979).
Lance et al., Biochemical and Biophysical Res. Comm., vol. 119, No. 1, pp. 265–272 (Feb. 1984).
Patchornik et al., Synthesis of Peptides by the Polymeric Reagent Approach, Perspectives in Peptide Chemistry, pp. 118–128 (1981).
Schiller, et al., Biochemical and Biophysical Research Communications, No. 143, vol. 2, pp. 499–505, Mar. 1987.
Rudinger, *Peptide Hormones* JA Parsons ed. (Univ. Park Press 1976) pp. 1–7.
Spatola, Chemistry and Biochemistry of Amino Acids, Peptides and Proteins, Boris Weinstein ed. (Marcell Dekkee Inc. 1983) pp. 267–357.
Breiopohl et al. Tetr. Lett. vol. 28, No. 46, pp. 5647–5650 (1987).

*Primary Examiner*—Michael L. Shippen
*Attorney, Agent, or Firm*—Finnegan, Henderson, Farabow, Garrett & Dunner, L.L.P.

[57] ABSTRACT

The invention relates to compounds of the formula I

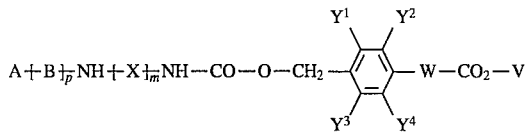

in which

A denotes hydrogen or an amino protective group, B denotes one or more amino acids, X denotes alkylene or aralkylene, $Y^1$, $Y^2$, $Y^3$ and $Y^4$ are identical or different and denote hydrogen, methyl, methoxy or nitro, V denotes hydrogen or a carboxyl protective group, W denotes —$[CH_2]_n$— or —O—$[CH_2]_n$—, m denotes 0 or 1, n denotes 0 to 6, and p denotes 0 to 5, to a process for their preparation. The compounds of formula I are useful as linkage agents or anchor groups in the solid-phase synthesis of peptide aminoalkylamides and peptide hydrazides.

5 Claims, No Drawings

SYNTHESIS OF PEPTIDE AMINOALKYLAMIDES AND PEPTIDE HYDRAZIDES BY THE SOLID-PHASE METHOD

CROSS REFERENCE TO RELATED APPLICATIONS

This application is a continuation of prior application Ser. No. 07/783,335 filed Oct. 28, 1992, now abandoned, which is a continuation-in-part of application Ser. No. 07/109,532 filed Oct. 19, 1987, abandoned, and is a continuation-in-part of application Ser. No. 07/218,798 filed Jul. 14, 1988, abandoned, and is a continuation-in-part of application Ser. No. 07/747,492 filed Aug. 19, 1991, abandoned, which is a continuation of application Ser. No. 07/284,874 filed Dec. 14, 1988, abandoned.

BACKGROUND OF THE INVENTION

The introduction of an aminoalkylamide into the C-terminal end of a biologically active peptide has in some cases had beneficial effects on the metabolic stability and activity (EP-A 179 332). The preparation of the peptides modified in this way has made use of the classical coupling of fragments in solution.

EP-A 179 332 reports the observation that simple dipeptides such as:

benzyloxycarbonyl-Lys-Phe-OMe cause the urge to groom and move in rats following intracerebroventricular (i.c.v.) administration of 10 μg. At the same time, cholinergic mechanisms in the central nervous system (CNS) are influenced. In the striatum of rats, the choline content is increased following subcutaneous (s.c.) administration of 10 μg. The effects are intensified if the carboxyl groups carries a radical with basic substituents, it being possible for lysine to be in the D-form. Thus, for example, the compound benzyloxycarbonyl-D-Lys-Phe-NH-$(CH_2)_8$-$NH_2$.2HCl shows the same action on i.c.v. or s.c. administration of 1 μg. The effects described are characteristic of ACTH and MSH.

EP-A 179 332 discloses novel peptides having an aminoalkylamino group bound to the C-terminal end of the peptide. These peptides are active on the central nervous system and act on the cholinergic system. As described in EP-A 179 332, these peptides effect a significant, dose-dependent weakening of the amnesia induced by electric shock or scopolamine in mice ("one-trial passive avoidance test"). The minimum effective dose, for example, required for the compound Met(O)-Glu-His-Phe-D-Lys-Phe-NH-$(CH_2)_8$-$NH_2$ is 0.03 μg/kg, following s.c. administration.

In humans, the peptides of EP-A 179 332 have a mood-lightening, antidepressant and anxiolytic action. These peptides increase attention to the environment, improve learning and memory performance, have a favorable effect on resocialization processes and can be used for all diseases of post-traumatic and degenerative brain damage which are associated with a reduced central acetylcholine metabolism function, for example, mild dementia and also early manifestations of Alzheimer's disease and the like.

In the solid-phase synthesis of peptides (see Patchornik, Cohen in Perspectives in Peptide Chemistry, pages 118–128 (Karger, Basle 1981)) the reactive chains are often not grafted directly onto the synthetic resin material, but are bonded to the carrier material by what are called spacers or links. The literature (for example Atherton, Sheppard in Perspectives in Peptide Chemistry, pages 101–117 (Karger, Basle 1981)) discloses, for example, reagents for introducing such spacers (called "linkage agents") which have the formulae VI, VII and VIII.

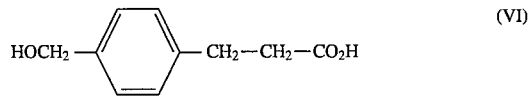

(VI)

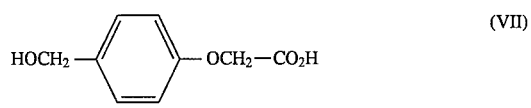

(VII)

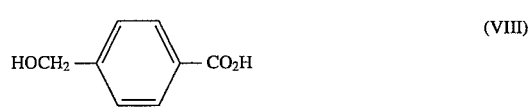

(VIII)

New linkage agents which allow direct construction, by solid phase synthesis, of peptides modified by C-terminal aminoalkylamide or hydrazide have been found.

Thus, the present invention relates to compounds of the formula I

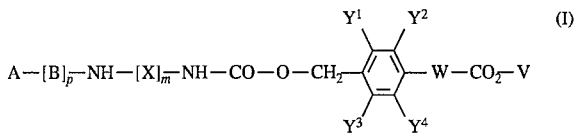

in which

A denotes hydrogen or an amino protective group which is labile to bases or labile to weak acids, B represents one or more, identical or different, amino acids, X denotes $(C_1-C_{12})$-alkylene or $(C_6-C_{10})$-aryl-$(C_1-C_{12})$alkylene, $Y^1$, $Y^2$, $Y^3$ and $Y^4$ are identical or different and denote hydrogen methyl, methoxy or nitro, at least one of these radicals denoting hydrogen, V denotes hydrogen or a carboxyl protective group, W denotes —$[CH_2]_n$— or —O—$[CH_2]_n$—, m is 0 or 1, n is an integer from 0 to 6, and p is an integer from 0 to 5.

The present invention relates to new linkage agents or anchor groups of the formula I. These compounds of formula I allow direct construction, by solid phase synthesis, of peptides modified by C-terminal amino-alkylamide or hydrazide. In the solid phase synthesis of peptides, the reactive amino acid chains are often not grafted directly onto the synthetic resin material, but are bonded to the carrier material by what are called linkage agents, anchor groups, or spacers. The compounds of formula I can be used in the synthesis of known or new peptides wherein they function as an anchor group during the solid phase synthesis of a peptide, then upon cleavage release a peptide having an aminoalkylamide or hydrazide end group. The Examples, infra, demonstrate the solid phase synthesis of such new useful peptides employing an anchor or spacer group according to formula I.

Preferred compounds of the formula I are those in which p is 0, 1 or 2, in particular, 0, and/or in which m is 1. Thus, for example, when p is 0, no amino acid B is present and when p is 1 only one amino acid B is present.

X is preferably —$[CH_2]_q$—, it being possible for q to be 1–12, preferably 1–8.

Preferably at least 2, in particular at least 3, of the radicals $Y_1$, $Y_2$, $Y_3$ and $Y_4$ denote hydrogen.

Protective groups which are labile to bases or labile to weak acids are, in particular, urethane protective groups, such as Fmoc, Ddz, Bpoc, Msc, Peoc, Pse and Tse, preferably Fmoc (see, for example, Hubbuch, Kontakte (Merck) 1979, No. 3, pages 14–23).

B represents one or more amino acids, preferably an α-amino acid, which, if chiral, can be present in the D or L form. When more than one amino acid is present, the amino acids are bound together by amide linkages as is known in amino acid and peptide chemistry. Preference is given to naturally occurring amino acids, their enantiomers, homologs, derivatives and simple metabolites, e.g. hydroxyproline, citruline, 4-hydroxymethylproline, N-ε-hydroxylysine or 4-methylglutamine acid. (See further, for example, Wunsch et al., Houben-Weyl 15/1 and 2, Stuttgart, Thieme 1974). The abbreviations used for the amino acids correspond to the three-letter code which is customary in peptide chemistry, and described in, for example, Europ. J. Biochem. 138, 9 (1984). Thus, for example, the following amino acids are suitable:

Aad, Abu, γ Abu, ABz, 2ABz, ε Aca, Ach, Acp, Adpd, Ahb, Aib, β Aib, Ala, β Ala, Δ Ala, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hCys, His, hSer, Hyl, Hyp, 3Hyp, Ile, Ise, Iva, Kyn, Lant, Lcn, Leu, Lsg, Lys, β Lys, Δ Lys, Met, Mim, Min, nArg, Nle, Nva, Oly, Orn, Pan, Pec, Pen, Phe, Phg, Pic, Pro, Δ Pro, Pse, Pya, Pyr, Pza, Qin, Ros, Sar, Sec, Sem, Ser, Thi, β Thi, Thr, Thy, Thx, Tia, Tle, Tly, Trp, Trta, Tyr, Val and the residues of the corresponding enantiomeric D-amino acids.

Functional groups in the side chains of the said amino acids can be in protected form. Suitable protective groups are described in Hubbuch, Kontakte (Merck) 1979, No. 3, pages 14–23, and in Bullesbach, Kontakte (Merck) 1980, No. 1, pages 23–35. The preferred groups are those which are stable to bases and weak acids and can be eliminated using strong acids.

Alkylene can be straight-chain or branched. Examples of definitions of $(C_6-C_{10})$-aryl are phenyl, tolyl or naphthyl; phenyl is preferred.

A carboxyl protective group V is, for example, $(C_1-C_6)$-alkyl or $(C_7-C_{11})$-aralkyl; preference is given to methyl, ethyl, tert.butyl, benzyl and modified benzyl, such as p-chloro-, p-bromo-, p-nitro- and p-methoxybenzyl and the nitrogen analog picolyl. In the wider sense, such protective groups include activated ester groups such as ONSu, OBt, OObt or p-nitrophenoxy.

The invention also relates to a process for the preparation of the compounds of the formula I, which comprises a) reaction of a compound of-the formula II

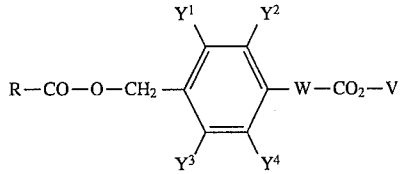

in which
R represents a leaving group which can be detached nucleophilically,
V represents a carboxyl protective group, and
W, $Y^1$, $Y^2$, $Y^3$ and $Y^4$ and are as defined above, with a compound of the formula III $$A\text{---}[B]_p\text{---}NH\text{---}[X]_m\text{---}NH_2 \qquad (III)$$

in which A represents an amino protective group which is labile to bases or labile to weak acids, and B, X, p and m are as defined above, and elimination of, where appropriate, one or both of the protective groups A and/or V in the resulting protected compound of the formula I, with the formation of the free $NH_2$ and/or $CO_2H$ group(s), the preferred processes being those in which V is selectively eliminated, for example by reductive cleavage with Zn/glacial acetic acid, or b) reaction of a compound of the formula I in which A denotes hydrogen, and B, X, $Y^1$, $Y^2$, $Y^3$, $Y^4$, V, W, m, n and p are as defined above, with a compound of the formula IV $$A\text{---}[B]_{s\text{-}p}\text{---}OH \qquad (IV)$$

in which A, B and p are as defined above, but A does not denote hydrogen, or its active ester, halide or azide, and, if V is not hydrogen, where appropriate elimination of a carboxyl protective group V with the formation of the carboxyl group.

A leaving group R which can be detached nucleophilically is, for example, halogen, such as chlorine, bromine and iodine, or activated aryloxy, such as p-nitrophenoxy.

The reaction of a compound of the formula II with a compound of the formula III is preferably carried out in an aprotic solvent such as, for example, THF, DMF, $CHCl_3$ or $CH_2Cl_2$, advantageously in the presence of a base such as, for example, a tertiary amine, for example ethyl triisopropylamine, triethylamine or pyridine, the addition of an acylation catalyst such as, for example, DMAP, HOObt or HOBt having an advantageous effect, at a temperature between 0° C. and the boiling point of the reaction mixture, preferably between 0° C. and 40° C.

Compounds of the formula I (A=hydrogen) are reacted with compounds of the formula IV, their active ester, halide or azide preferably in an organic solvent, such as DMF, advantageously in the presence of a base such as, for example, a tert.amine, at a temperature between −10° C. and the boiling point of the reaction mixture, preferably at room temperature. Examples of suitable active esters are the ONSu, OBt, OObt and p-nitrophenoxy compounds. Preferred halogen derivatives are the chlorides. Pyridinium perchlorate can be added to improve the solubility.

Compounds of the formula II are prepared by, for example, reacting esters of the formula IX

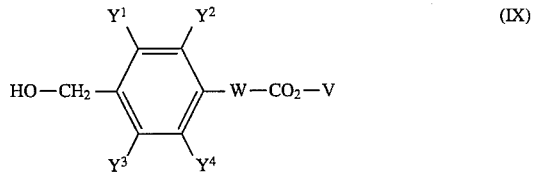

in which $Y^1$, $Y^2$, $Y^3$, $Y^4$, W and V are as defined above, but V does not denote hydrogen, with phosgene or phosgene derivatives such as, for example, nitrophenyl chloroformate in an aprotic polar solvent, for example THF or DMF, mixed with a tert. base, for example a tert. amine such as pyridine, preferably in the ratio 1:1, at a temperature between −40° C. and room temperature, preferably between −20° C. and 0° C.

The invention also relates to the use of a compound of the formula I, in which V denotes hydrogen and A does not denote hydrogen, in the solid-phase synthesis of compounds of the formula V:

P—NH—[X]$_m$—NH$_2$ (V)

in which P represents a peptide residue comprising q≦p+1 α-amino acids, and X, m and p are as defined above, and to a process for the preparation of a peptide of the formula V, in which P, X, m and p are as defined above, by solid-phase synthesis, which comprises coupling a compound of the formula I, in which A does not denote hydrogen, and V represents hydrogen, to a resin, eliminating the protective group A, stepwise coupling on q-p α-amino acids which are, where appropriate, in the form of their activated derivatives and which have been temporarily protected by amino protective groups which are labile to bases or labile to weak acids and, after construction is complete, liberating the peptide from the resin by treatment with a moderately strong to strong acid, the temporarily introduced side-chain protective groups being eliminated again at the same time or, by suitable measures, subsequent thereto.

If necessary to prevent side reactions or for the synthesis of specific peptides, the functional groups in the side chain of amino acids are additionally protected by suitable protective groups (see, for example, T. W. Greene, "Protective Groups in Organic Syntheses", New York, John Wiley & Sons, 1981), those primarily used being Arg(Tos), Arg(Mts), Arg(Mtr), Asp(OBzl), Asp(OBut), Cys(4-MeBzl), Cys(Acm), Cys(SBut), Glu(OBzl), Glu(OBut), His(Tos), His(Fmoc), His(Dnp), His(Trt), Lys(Cl-2), Lys(Boc), Met(O), Ser(Bzl), Ser(But), Thr(Bzl), Thr(But).

The resins used as carrier material are commercially available. BHA and MBHA resins are preferred.

The peptide of the formula V is then cleaved off by treatment with the moderately strong to strong acids customarily used in peptide synthesis (for example trifluoracetic acid and HF), there being cleavage of the urethane protective group contained in the spacer.

It is possible to use as coupling reagent for the compound of the formula I (V=H) and the other amino acid derivatives all possible activating reagents used in peptide synthesis, see, for example, Houben-Weyl, Methoden der organischen Chemie (Methods of organic chemistry), volume 15/2, but in particular carbodiimides such as, for example, N,N'-dicyclohexylcarbodiimide, N,N'-diisopropylcarbodiimide or N-ethyl-N'-(3-dimethylaminopropyl)carbodiimide. This coupling can be carried out directly by addition of the amino acid derivative with the activating reagent and, where appropriate, an additive which suppresses racemization, such as, for example, 1-hydroxybenzotriazole (HOBt) (W. Konig, R. Geiger, Chem. Ber. 102., 708 (1970)) or 3-hydroxy-4-oxo-3,4-dihydroxybenzotriazine (HOOBt) (W. Konig, R. Geiger, Chem. Ber. 103, 2054 (1970)) to the resin, or the preactivation of the amino acid derivative can be carried out separately as the symmetric anhydride or HOBt or HOObt ester, and the solution of the activated species in a suitable solvent can be added to the peptide-resin which is ready for coupling.

The coupling and activation of the compound of the formula I (V=H) and of the amino acid derivatives with one of the abovementioned activating reagents can be carried out in dimethylformamide or methylene chloride or a mixture of the two. The activated amino acid derivative is normally used in a 1.5- to 4-fold excess. In cases where incomplete coupling occurs, the coupling reaction is repeated, without previously carrying out the deblocking of the α-amino group of the peptide-resin which is necessary for coupling the next amino acid in the sequence.

Successful completion of the coupling reaction can be checked using the ninhydrin reaction as described, for example, by E. Kaiser et al. Anal. Biochem. 34,595 (1970).

The synthesis can also be carried out automatically, for example using an Applied Biosystems model 430A peptide synthesizer, it being possible to use either the synthesis programs provided by the apparatus manufacturer or those constructed by the user himself. The latter are particularly employed when amino acid derivatives protected with the Fmoc group are used.

When the peptide amides are cleaved off the resin with hydrogen fluoride and trifluoroacetic acid, it is customary to add substances as cation traps, such as phenol, cresol, thiocresol, thioanisole, anisole, ethanedithiol, dimethyl sulfide, ethyl methyl sulfide or a mixture of two or more of these auxiliaries. In this connection, the trifluoroacetic acid can also be used diluted by suitable solvents such as, for example, methylene chloride.

Abbreviations used:

| | |
|---|---|
| Fmoc | 9-fluorenylmethyloxycarbonyl |
| Ddz | α,α-dimethyl-3,5-dimethoxybenzyloxycarbonyl |
| Bpoc | 2-[4-biphenylyl]-2-propyloxycarbonyl |
| Msc | Methylsulfonylethyloxycarbonyl |
| Peoc | pyridylethyloxycarbonyl |
| Pse | phenylsulfonylethyloxycarbonyl |
| Tse | tolylsulfonylethyloxycarbonyl |
| HONSu | N-hydroxysuccinimide |
| HOBt | 1-hydroxybenzotriazole |
| HOObt | 3-hydroxy-4-oxo-3,4-dihydrobenzotriazine |
| THF | tetrahydrofuran |
| DMF | dimethylformamide |
| DMAP | dimethylaminopyridine |
| Acm | Acetamidomethyl |
| ε-Ahx | ε-Aminohexanoyl |
| Aoc | cis, endo-2-Azabicyclo[3.3.0]octane-3-S-carbonyl |
| Boc | tert.-Butyloxycarbonyl |
| But | tert.-Butyl |
| Bzl | Benzyl |
| Cl-z | 4-Chlorobenzyloxycarbonyl |
| Dnp | 2,4-Dinitrophenyl |
| Mac | Mercaptoacetic acid |
| Mbu | Mercaptobutyric acid |
| Me | Methyl |
| 4-Mebzl | 4-Methylbenzyl |
| Mpr | Mercaptoproprionic acid |
| Mtr | 4-Methoxy-2,3,6-trimethylphenylsulfonyl |
| Mts | Mesitylene-2-sulfonyl |
| TFA | Trifluoroacetic acid |
| Tcs | 4-Methylphenylsulfonyl |
| Trt | Trityl |
| Aad | α-aminoadipic acid |
| γAbu | γ-aminobutyric acid |
| AC | acetyl |
| BHA | benzhydrylamino |
| hArg | homoarginine |
| MBHA | methylbenzhydrylamino |
| Mtr | 4-methoxy-2,3,6-trimethylphenylsulfonyl |
| Nle | norleucine |
| NMP | N-methylpyrrolidone |
| Tic | 3-carboxy-1,2,3,4-tetrahydroisoquinoline |

The examples which follow serve to illustrate the present invention without intending to confine it to them.

EXAMPLE 1

Methyl 4-hydroxymethylphenoxyacetate 18.2 g of 4-hydroxymethylphenoxyacetic acid are dissolved together with 17.1 ml of N,N-diisopropylethylamine in 50 ml of DMF, and then 6.1 ml of methyl iodide are added to the stirred solution. The mixture warms slightly during this. The reaction is complete after 3 h. The solvent is removed in vacuo. The residue is taken up in ether, and the solution is extracted once with 0.5 N hydrochloric acid. The aqueous phase is then extracted three times with ether, and the combined ether phases are washed with aqueous sodium bicarbonate solution and concentrated. The residue is dissolved in ethyl acetate and filtered through a short silica gel column. The pale yellowish oil which is obtained after concentration crystallizes on being left to stand.

NMR and mass spectrum are consistent with the indicated structure.

EXAMPLE 2

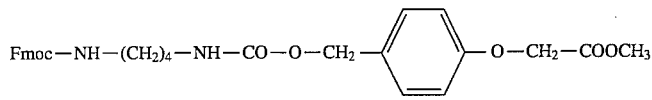

9.8 g of methyl 4-hydroxymethylphenoxyacetate are dissolved in 200 ml of dry $CH_2Cl_2$, and then 10.1 g of p-nitro-phenyl chloroformate and 7 ml of triethylamine are added. The mixture is boiled under reflux for about 6 h, until the precursor has completely reacted. Then a suspension of 15.5 g of Fmoc-NH-$(CH_2)_4$-$NH_2$ (prepared by reaction of Boc-NH-$(CH_2)_4$-$NH_2$ with Fmoc-ONSu followed by elimination of Boc) in 100 ml of dry $CH_2Cl_2$ and a further 7 ml of triethylamine are added, and the mixture is boiled under reflux. After the reaction is complete, the solvent is removed in vacuo, and the residue is digested with ether and filtered off with suction. The residue on the filter is washed with aqueous 1N $Na_2CO_3$ solution and then with hot water, and is dried under high vacuum in a desiccator.

Melting point 122°–124° C., NMR and mass spectrum are consistent with the indicated structure.

EXAMPLE 3

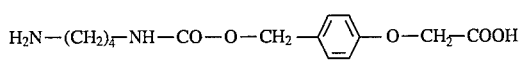

5.2 g of the ester obtained as in Example 2 are suspended in 100 ml of methanol, and 6 equivalents of an aqueous 1N NaOH solution are added. After the reaction is complete, the pH is adjusted to 3 with aqueous 1N HCl, and the methanol is removed in vacuo. The precipitate is filtered off with suction, washed with a little $H_2O$, and then digested in ether and again filtered with suction.

Melting point starts at 196° C. (decomposition), NMR and mass spectrum are consistent with the indicated structure.

EXAMPLE 4

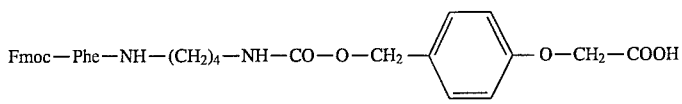

1.5 g of the product obtained as in Example 3 are suspended in 50 ml of dry DMF. Then, successively, 0.9 g of pyridinium perchlorate (to improve the solubility) and 2.6 g of Fmoc-Phe-OObt and 0.5 ml of triethylamine are added. The mixture is stirred at room temperature. After the reaction is complete, the solvent is removed in vacuo, and the residue is partitioned between ethyl acetate and $H_2O$. The aqueous phase is extracted once more with ethyl acetate, and the combined organic phases are dried and concentrated. The residue is digested with a little $CHCl_3$ and is filtered off with suction. The residue on the filter is washed with a little ether and is dried.

Melting point starts at 140° C. (decomposition), NMR and mass spectrum are consistent with the indicated structure.

EXAMPLE 5

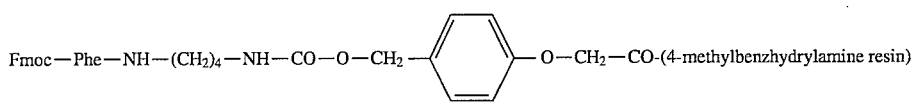

1.4 g of the Fmoc-phenylalanine spacer acid obtained as in Example 4 are dissolved together with 350 mg of HOBt in 40 ml dry DMF, and the solution is added to 3.66 g of 4-methylbenzhydrylamine resin (Nova Biochem, loading 0.4 mmol/g). Then 0.6 ml of diisopropylcarbodiimide is added, and the reaction is allowed to go to completion, mixing continuously. After the reaction is complete, the product is filtered off with suction, washed with DMF, isopropanol, $CH_2Cl_2$ and tert.-butyl methyl ether and is dried under high vacuum. Loading according to elemental analysis (nitrogen determination): 0.3 mmol/g.

EXAMPLE 6

Synthesis of [des-Tyr[24] des-Arg[23]]-r-atriopeptinIII-(4-amino)butylamide

The structure of the title peptide is as follows. The peptide has diuretic and saluretic biological activity.

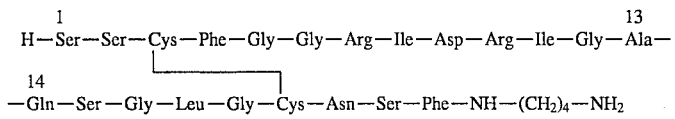

The peptide synthesis is carried out on 1 g of the above-mentioned resin in Example 5 using OOBt esters of Fmoc-amino acids with an Applied Biosystems model 430A automatic peptide synthesizer and synthesis programs modified by ourselves.

For this, 1 mmol of each of the appropriate amino acid derivatives is weighed into the cartridges supplied by the manufacturer; Fmoc-Arg(Mtr)-OH, Fmoc-Asn-OH and Fmoc-Gln-OH are weighed together with 1.5 mmol of HOBt into the cartridges. These amino acids are preactivated directly in the cartridges by dissolving in 4 ml of DMF and adding 2 ml of a 0.55 M solution of diisopropylcarbodiimide in DMF. The HOObt esters are dissolved in 6 ml of DMF and then pumped, in the same way as the amino acids arginine, asparagine and glutamine which are preactivated in situ, onto the resin which has previously been deblocked with 20% piperidine in DMF. The amino acids which are activated in situ are coupled twice.

After the synthesis is complete, the peptide butylamide is cleaved off the resin, simultaneously removing the side-chain protective groups with trifluoroacetic acid which contains thioanisole and m-cresol as cation traps. The residue obtained after removal of the trifluoroacetic acid in vacuo is subjected to digestion with ethyl acetate and centrifugation several times. The remaining crude peptide is treated with tributylphosphine in trifluoroethanol to remove the cysteine protective group.

After the solvent has been removed, the residue is again digested with ethyl acetate and centrifuged. The reduced crude peptide is immediately oxidized with iodine in 80% strength aqueous acetic acid, the excess $I_2$ is removed with ascorbic acid, and the reaction mixture is concentrated to a small volume and then salt is removed on ®Sephadex G25 with aqueous 1 N acetic acid. The fractions containing the pure peptide are combined and freeze-dried.

According to amino acid analysis, the amino acid composition of the peptide corresponds to the indicated formula.

using Fmoc-amino acid OObt esters and an Applied Biosystems model 430A automatic peptide synthesizer and synthesis programs modified by applicants. The resin is the 4-methylbenzhydrylamine resin mentioned above in Example 5.

The synthesis entails 1 mmol each of the appropriate amino acid derivatives being weighed into cartridges supplied by the manufacturer; FMOC-Arg(Mtr)-OH, Fmoc-Asn-OH and Fmoc-Gln-OH are weighed together with 1.5 mmol of HOBt into the cartridges. These amino acids are preactivated directly in the cartridges by dissolving in 4 ml of DMF and adding 2 ml of a 0.55 M solution of diisopropylcarbodiimide in DMF. The HOObt esters of the other amino acids are dissolved in 6 ml of DMF and then pumped, in the same way as the amino acids argenine, aspargine and glutamine which are preactivated in situ, onto the resin which has previously been unblocked with 20% piperidine in DMF. The amino acids which are activated in situ are coupled twice.

After the synthesis is complete, the peptide octyl amide is cleaved off the resin, simultaneously removing the side-chain protective groups, using trifluoracetic acid which contains thioanisole and m-cresol as cation traps. The residue obtained after removal of the trifluoroacetic acid in vacuo is digested with ethyl acetate and centrifuged several times. The remaining crude peptide is treated with tributylphosphoine in trifluoroethanol to remove the cysteine protective group. After removal of the solvent, the residue is again digested with ethyl acetate and centrifuged. The reduced crude peptide is immediately oxidized with iodine in 80% strength aqueous acetic acid, the $I_2$ excess is removed with ascorbic acid, and the reaction mixture is concentrated to a small volume, and then salts are removed on ®Sephadex G25 using aqueous 1N acetic acid. The fractions containing pure peptide are combined and freeze-dried.

EXAMPLE 6A-1

Synthesis of H-Aoc-Ser—Cys—Phe—Gly—Gly—Arg—Ile—Asp—Arg—Ile—Gly—Ala—
                     |_____
                     Gln—Ser—Gly—Leu—Gly—Cys—Asn—Ser—Phe—NH—(CH$_2$)$_8$—NH$_2$ The peptide is synthesized on 1 g of the resin with the structure:

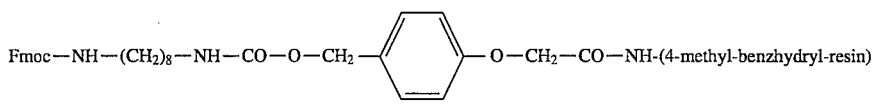

EXAMPLE 6A-2

Synthesis of H-Aoc-Ser—Cys—Phe-D-Ala—Gly—Arg—Ile—Glu—Arg—Ile—Gly—Ala—
Gln—Ser—Gly—Leu—Gly—Cys—Gly-D-Ala—Phe—NH—(CH$_2$)$_6$—NH$_2$ The peptide is synthesized on 1 g resin with the structure

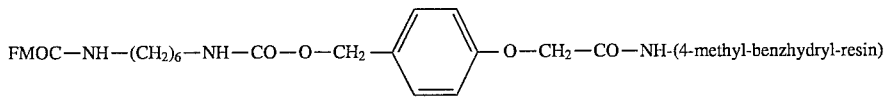

using Fmoc-amino acid OObt esters according to Example 6A-1.

EXAMPLE 6A-3

Synthesis of H-Aoc-Ser—Cys—Phe-D-Ala—Gly—Arg—Ile—Glu—Arg—Ile—Ala—Ala—
Thr—Ser—Gly—Leu—Gly—Cys—Pro—Ser—Phe—NH—(CH$_2$)$_4$—NH$_2$ The peptide is synthesized on 1 g resin with the structure

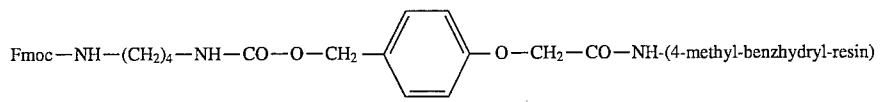

using Fmoc-amino acid 00bt esters according to example 6A-1.

The peptides were characterized by amino acid analysis. The peptides were hydrolyzed using 6 N hydrochloric acid at 120° C. for 12 hours. In this, cysteine resulted in a mixture of cysteine and cysteic acid and was present in all the peptides.

| Peptide | 6A-1 | 6A-2 | 6A-3 |
|---------|------|------|------|
| ASP | 1.93 | | |
| THR | | | 1.06 |
| BER | 2.39 | 1.03 | 2.29 |
| GLU | 1.10 | 2.05 | 1.00 |
| PRO | | | 1.13 |
| GLY | 5.08 | 4.90 | 2.98 |
| ALA | 1.05 | 2.84 | 2.85 |
| ILE | 1.79 | 1.87 | 1.93 |
| LEU | 0.97 | 1.00 | 1.04 |
| TYR | | | |
| PHE | 1.97 | 1.83 | 1.83 |
| LYS | | | |
| ARG | 2.00 | 1.80 | 1.81 |

The peptides 6A-1 3 are analogs of ANF (atrial natriuretic factor), a peptide which is formed in the atrium of mammalian hearts and has natriuretic, diuretic and vasoactive effects (Currie et al. Science 223, 67 1984: Kangawa, Matsuo, Biochem. Biophys. Res. Commun. 118, 131 1984). It is possible by the modifications according to the invention to enhance or change specifically the effects of ANF. Thus, for example, the duration of action and profile of action of the natriuretic properties can be beneficially affected, or the vasoactive effect can be diminished, or even the opposite effect can be achieved. Furthermore, the peptides according to the invention have immunomodulating properties which have not previously been described for peptides isolated from the atria of mammalian hearts.

The receptor-binding assay described hereinafter is used to investigate the binding power necessary for the biological effect of peptides 6A-1, 6A-2, and 6A-3 which are synthesized by aid of a compound according to this invention as described above.

Preparations of membranes from the bovine adrenal cortex

Fresh bovine adrenals were obtained from a slaughterhouse and transported on ice. After the adrenal medulla had been removed, the cortex was cut into small pieces with scissors in ice-cold buffer A (5 mmol/l Tris, 1 mmol/l MgCl$_2$, 250 mmol/l sucrose, pH 7.4, at 0° C.). The tissue was homogenized in buffer A in a ®Waring blender. Larger particles were removed by subsequent filtration through a gauze, and the filtrate was rehomogenized in a Potter homogenizer with 20 strokes. Thereafter, the cell particles of higher density were removed in a 10-minute centrifugation at 3000 x g and 4° C. and were discarded. The plasma membranes in the supernatant were then removed at 39,000 x g for 10 minutes and resuspended in buffer B (75 mmol/l Tris, 35 mmol/l MgCl$_2$, pH 7.4 at 4° C.). After this centrifugation step had been repeated twice, the plasma membranes were taken up in buffer B containing 250 mmol/l sucrose and were frozen in portions corresponding to 1 g of original cortex tissue/ml in liquid nitrogen. On subsequent storage at −70° C., no decrease in the binding activity was found over several months.

Receptor binding

For the binding experiments, the membranes were thawed, centrifuged at 39,000 x g for 10 minutes and suspended in buffer C (100 mmol/l NaCl, 0.1 mmol/l EDTA-Na$_2$, 50 mmol/l HEPES, pH 7.4, and 0.2% bovine serum albumin to reduce adsorption to the walls). 40 μmol/l aprotinin, a peptidase inhibitor, were added to the plasma membrane suspension to prevent breakdown of the radiolabeled ligand (radioligand) during the incubation time. The binding experiment was carried out in micro titer plates at 25° C. with 60 minutes to equilibrium. Binding was started by addition of the membrane suspension. The final volume of each sample was 250 μl. These contained about 14,000 cpm of the radioligand ($^{125}$I-human atrial natriuretic peptide$_{1-28}$ from Amersham Buchler, FRG) with a specific activity of 74 TBq/mmol and a quantity of the membrane protein which had bound about 50% of the added radioligand. Free and bound radioligand were separated by rapid filtration through a ®Whatman GF/C glass fiber filter using a ®Skatron cell harvester. In order to reduce the non-specific binding, the filters had previously been placed for 1 hour in freshly prepared 3% strength polyethyleneimine at pH 10. After the filtration, the amount of the radioligand retained on the filters was measured in a gamma scintillation counter. The nonspecific binding was defined as the binding in the presence of 0.5 μmol/l atriopeptin III Binding data (atriopeptin III displacement)

| Example No. | IC$_{50}$ [nm] substance | IC$_{50}$ [nm] atriopeptin III |
|---|---|---|
| 6A-1 | 2.40 | 8.50 |
| 6A-2 | 1.40 | 3.50 |
| 6A-3 | 0.48 | 5.40 |

The vasorelaxant effect of peptides 6A 1-3 was tested in vitro on strips of guinea pig aorta which had previously been contracted with 25 mM KCl. The diuretic and natriuretic effect was demonstrated in vivo by i.v. administration to anesthetized rats. Atriopeptin III was used for comparison.

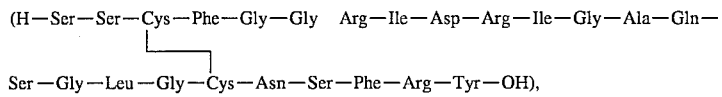

(H—Ser—Ser—Cys—Phe—Gly—Gly Arg—Ile—Asp—Arg—Ile—Gly—Ala—Gln—
Ser—Gly—Leu—Gly—Cys—Asn—Ser—Phe—Arg—Tyr—OH), an amount which suffices completely to displace the radioligand from the receptors.

Calculation of the data

The IC$_{50}$ values represent the concentration of the test substance which is necessary to inhibit 50% of the binding of the radioligand. The values were calculated from the measured values using the median effect equation of Chen (1976), J. Theor. Biol. 59, 253–276, with a microcomputer.

The new peptides 6A-1, 6A-2, and 6A-3 have, individually or in combination, diuretic, saluretic, vasorelaxant and immunomodulating effects, or can be used in cases of chronic or/and acute renal insufficiency and for protection of the kidney from nephrotoxic substances, for example cyclosporin, especially in cases of renal transplantation. The peptides 6A-1, 6A-2, and 6A-3 are also useful for the treatment of glaucoma and/or for reducing the intraocular pressure in mammals, preferably in humans, by topical or systemic administration thereof.

EXAMPLE 6B

Synthesis of
[D-Ala2,Nle27]-GRF(1-28)-6-aminohexylamide
with the sequence, 6B-1.

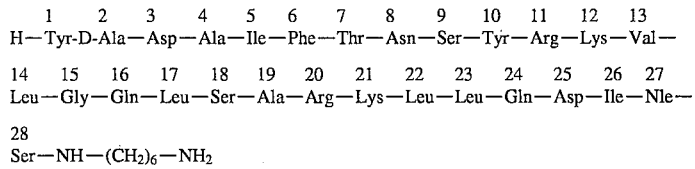

1  2    3   4   5   6   7   8   9   10  11  12  13
H—Tyr-D-Ala—Asp—Ala—Ile—Phe—Thr—Asn—Ser—Tyr—Arg—Lys—Val—

14  15  16  17  18  19  20  21  22  23  24  25  26  27
Leu—Gly—Gln—Leu—Ser—Ala—Arg—Lys—Leu—Leu—Gln—Asp—Ile—Nle—

28
Ser—NH—(CH$_2$)$_6$—NH$_2$

The peptide synthesis was carried out on 1 g of an aminomethyl-resin which had been modified with an anchor group according to formula I:

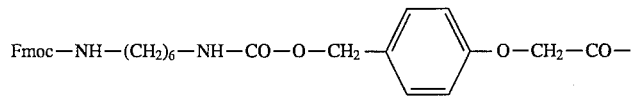

Fmoc—NH—(CH$_2$)$_6$—NH—CO—O—CH$_2$—⟨phenyl⟩—O—CH$_2$—CO— using Fmoc-amino acid OOBt esters with an automatic peptide synthesizer (Applied Biosystems model 430A) and synthesis programs modified by us. For this purpose, 1 mmol of each of the appropriate amino acid derivatives was weighed into the cartridges provided by the manufacturer, and Fmoc-Arg(Mtr)-OH, Fmoc-Asn-OH and Fmoc-Gln-OH were weighed into the cartridges together with 0.95 mmol of HOObt. These amino acids were previously activated directly in the cartridges by dissolving in 4 ml of DMF and adding 2 ml of a 0.55 M solution of diisopropylcarbodiimide in DMF. The HOObt esters of the other amino acids were dissolved in 6 ml of NMP and then coupled, in just the same way as the amino acids arginine, asparagine and glutamine which had previously been activated in situ, to the resin which had previously been deblocked with 20% piperidine in DMF, with the amino acids which had been activated in situ being coupled twice. After the synthesis was complete, the peptide 6-aminohexylamide was eliminated from the resin, simultaneously removing the side-chain protective groups, with trifluoroacetic acid which contained thioanisole and m-cresol as cation traps. The residue obtained after removal of the trifluoroacetic acid in vacuo was digested with ethyl acetate, and centrifuged, several times. The remaining crude peptide was chromatographed on ®Sephadex G25 with 1 N acetic acid. The fractions containing the pure peptide were combined and freeze-dried.

The peptide of the formula 6B-1 brings about the release of growth hormone in the pituitary. The peptide of the formula 6B-1 can also be employed in veterinary medicine or to accelerate growth in animal breeding and to increase milk output.

The methods for the determination of the biological activity of GRF peptides are indicated, for example, in L. Frohman, J. Jansson, Endocrine Reviews 7 (1986) 223. The in vitro assay was carried out by incubation of pituitaries from male rats with a solution of the particular peptide in various concentrations. The growth hormone content of the pituitaries and of the medium was determined by a radioimmunoassay by the method described by D. S. Schalch, S. Reichlin, Endocrinology 79 (1966) 275. The in vivo assay was carried out on urethane-anesthetized male rats by i.v. injection of peptide solutions in various concentrations. The plasma concentration of growth hormone was determined by radioimmunoassay as described above. The GH response was expressed in terms of MIAMD-rat-GH. The minimal effective doses were reported:

| Results: Minimal Effective Dose | |
|---|---|
| Example | in vivo |
| 6B-1 | 20 ng |

The peptide 6B-1 exhibits a GRF action (release of growth hormone) in the body which substantially corresponds in quantitative terms to that of natural GRF or of the corresponding analogs. The dose to be used in human and/or veterinary medicine thus also corresponds to the dose to be used in each case for GRF or its analogs, taking into account the specific strength of biological action of these compounds.

The methods for the determination of the biological activity of GRF peptides are indicated, for example, in L. Frohman, J. Jansson, Endocrine Reviews 7 (1986) 223. The in vitro assay was carried out by incubation of pituitaries from male rats with a solution of the particular peptide in various concentrations. The growth hormone content of the pituitaries and of the medium was determined by a radioimmunoassay by the method described by D. S. Schalch, S. Reichlin, Endocrinology 79 (1966) 275. The in vivo assay was carried out on urethane-anesthetized male rats by i.v. injection of peptide solutions in various concentrations. The plasma concentration of growth hormone was determined by radioimmunoassay as described above.

EXAMPLE 7

Phenacyl 4-hydroxymethylphenoxyacetate 182 g of 4-hydroxymethylphenoxyacetic acid and 199 g of α-bromoacetophenone are dissolved in 600 ml of dry DMF, and then, at 0° C., 138 ml of triethylamine are rapidly added dropwise. The mixture is allowed to reach room temperature, and is stirred overnight. The DMF solution is poured into 3.5 l of water, and the aqueous phase is extracted with ethyl acetate. The organic phase is washed with water, dried over sodium sulfate and concentrated. The product precipitates out on evaporation. It is filtered off with suction, washed with ethyl acetate/n-hexane 1:1 and dried under high vacuum.

Melting point: 94°–95° C. NMR is consistent with the indicated structure.

EXAMPLE 8

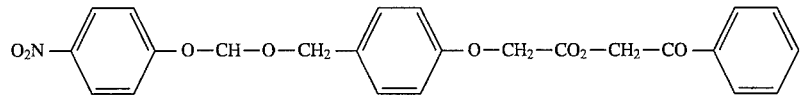

30 g of phenacyl 4-hydroxymethylphenoxyacetate are dissolved, under protective gas, in 500 ml of a 1:1 mixture of THF and pyridine, and the solution is cooled to −20° C. Then 21 g of p-nitrophenyl chloroformate dissolved in 100 ml of THF are added dropwise. After the mixture has been stirred at this temperature for 30 minutes, it is allowed to warm to 0° C. and stirred into 1 l of a half-saturated aqueous NaCl solution at 0° C, and the mixture is then stirred for 30 minutes. The precipitate is filtered off with suction, washed with ice-water and, after drying, triturated with n-hexane.

Melting point: 142°–145° C., NMR is consistent with the indicated structure.

EXAMPLE 9

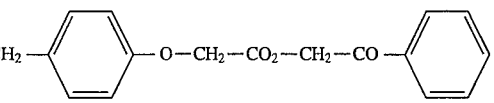

9.3 g of the compound prepared in Example 8, 12.25 g of Fmoc-Phe-NH-(CH$_2$)$_8$-NH$_2$ trifluoroacetate and 3.26 g of HOObt are placed as the solid substances in a flask, and then a mixture of 2.58 g of ethyl diisopropylamine in 100 ml of dry DMF is poured over. The mixture is then stirred at 40° C. for 3.5 hours and then stirred into 500 ml of half-saturated aqueous NaCl solution. The precipitate which separates out is filtered off with suction, washed with ice-water and, after drying, triturated with ether/ethyl acetate.

Melting point: 147°–150° C., NMR and MS are consistent with the indicated formula.

The following compounds (Examples 10 to 14) are prepared in analogy to Example 9:

EXAMPLE 10

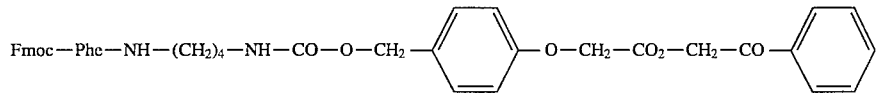

Melting point 144°–147° C., NMR and MS correspond to the indicated formula.

EXAMPLE 11

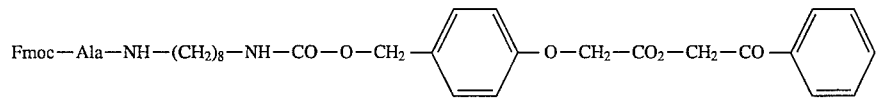

Melting point 179°–181° C. NMR and MS correspond to the indicated formula.

EXAMPLE 12

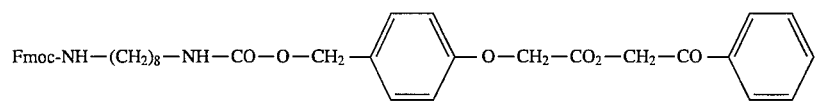

Melting point 144°–145° C., NMR and MS correspond to the indicated formula.

EXAMPLE 13

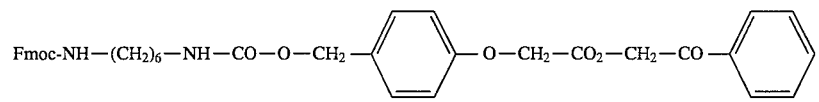

Melting point 172°–175° C., NMR corresponds to the indicated formula.

EXAMPLE 14

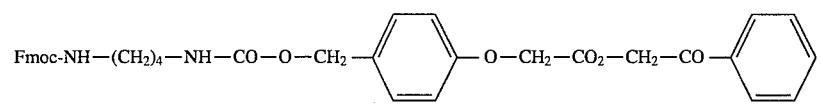

Melting point 165°–166° C., NMR corresponds to the indicated formula.

EXAMPLE 15

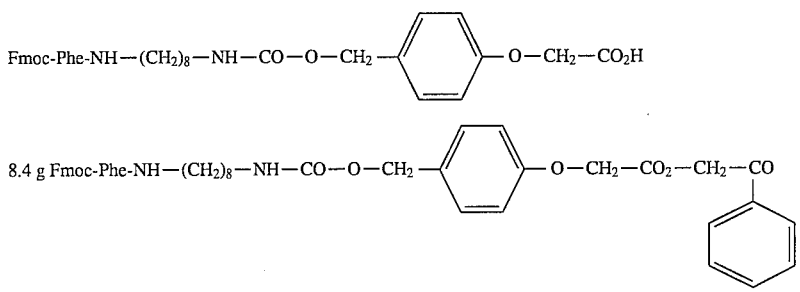

are suspended in a mixture of 150 ml of glacial acetic acid and 50 ml of dichloromethane, and 12 g of zinc powder which has previously been activated by washing with 1N HCl and dry ethanol are added in portions. After a few minutes, the suspension becomes more viscous and difficult to stir, while there is slight evolution of heat. Hence a further 80 ml of glacial acetic acid and 50 ml of dichloromethane are added, and stirring is continued overnight. The mixture is then filtered with suction through a filter with a clarifying layer, washing with glacial acetic acid and dichloromethane. The filtrate is concentrated, and the oil which remains as residue is taken up in a little dichloromethane and stirred with ethyl acetate and ether. The precipitated product is filtered off with suction and dried under high vacuum. Melting point: decomposition above 160° C., NMR and MS are consistent with the indicated formula.

In addition, the compounds of Examples 16 to 18, 22 and 23 are prepared by the method described in Example 15:

EXAMPLE 16

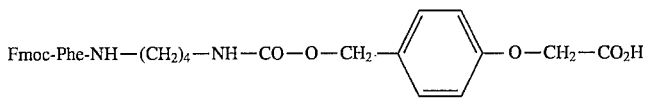

Melting point: decomposition above 150° C., NMR and MS are consistent with the indicated formula.

EXAMPLE 17

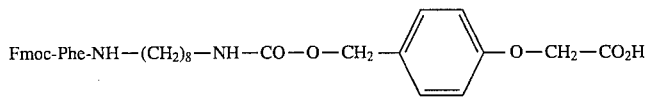

Melting point: decomposition above 160° C., NMR and MS are consistent with the indicated formula.

EXAMPLE 18

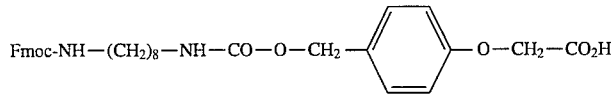

Melting point: decomposition above 154° C., NMR and MS are consistent with the indicated formula.

EXAMPLE 19

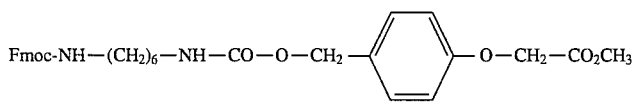

The synthesis is carried out in analogy to Example 2. Melting point: 115°–118° C., NMR and MS are consistent with the indicated formula.

EXAMPLE 20

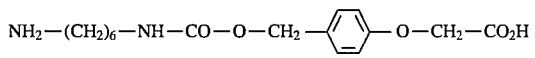

was prepared by the method described in Example 3. Melting point: 184°–187° C. decomposition, NMR and MS are consistent with the indicated formula.

EXAMPLE 21

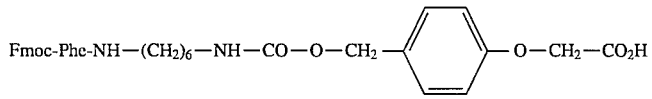

The synthesis is carried out in analogy to Example 4. Melting point: decomposition above 120° C., NMR and MS are consistent with the indicated formula.

EXAMPLE 22

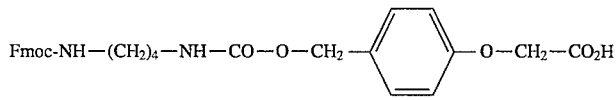

Melting point: decomposition above 158° C., NMR and MS are consistent with the indicated formula.

EXAMPLE 23

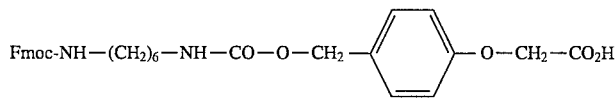

Melting point: decomposition above 142° C., NMR and MS are consistent with the indicated formula.

EXAMPLE 24

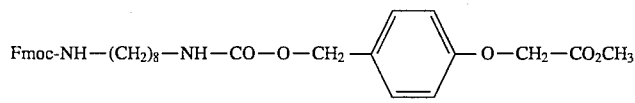

The synthesis is carried out in analogy to Example 2. Melting point: 117°–120° C., NMR and MS are consistent with the indicated formula.

EXAMPLE 25

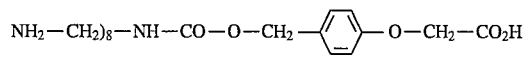

was prepared by the method described in Example 3. Melting point: 193°–195° C. decomposition, NMR and MS are consistent with the indicated formula.

We claim:

1. A compound of the formula

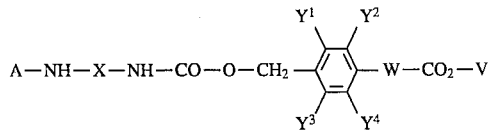

in which

A denotes hydrogen or an amino protective group which is labile to bases or labile to weak acids, X denotes $(C_1-C_{12})$-alkylene $Y^1$, $Y^2$, $Y^3$ and $Y^4$ are identical or different and denote hydrogen, methyl, methoxy or nitro, at least one of these radicals denoting hydrogen, V denotes hydrogen or a carboxyl protective group, W denotes $-[CH_2]_n-$ or $-O-[CH_2]_n-$, and n is an integer from 0 to 6.

2. The compound of claim 1, wherein X denotes $(C_4-C_8)-$ alkylene.

3. A compound as claimed in claim 1, in which X denotes $(C_1-C_{12})$-alkylene.

4. A compound as claimed in claim 3, in which X is a $(C_1-C_8)$-alkylene.

5. A compound as claimed in claim 1, in which at least 2 of the radicals $Y^1$, $Y^2$, $Y^3$ and $Y^4$ denote hydrogen.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Ser  Cys  Phe  Gly  Gly  Arg  Ile  Asp  Arg  Ile  Gly  Ala  Gln  Ser  Gly
1              5                        10                       15
Leu  Gly  Cys  Asn  Ser  Phe
                20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ser  Cys  Phe  Gly  Gly  Arg  Ile  Asp  Arg  Ile  Gly  Ala  Gln  Ser  Gly  Leu
1              5                        10                       15
Gly  Cys  Asn  Ser  Phe
                20
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Cys  Phe  Ala  Gly  Arg  Ile  Glu  Arg  Ile  Gly  Ala  Gln  Ser  Gly  Leu  Gly
1              5                        10                       15
Cys  Gly  Ala  Phe
                20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Cys  Phe  Ala  Gly  Arg  Ile  Glu  Arg  Ile  Ala  Ala  Thr  Ser  Gly  Leu  Gly
1              5                        10                       15
```

```
        Cys  Pro  Ser  Phe
                       20
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ser  Ser  Cys  Phe  Gly  Gly  Arg  Ile  Asp  Arg  Ile  Gly  Ala  Gln  Ser  Gly
1                   5                        10                       15

Leu  Gly  Cys  Asn  Ser  Phe  Arg  Tyr
                    20
```

( 2 ) INFORMATION FOR SEQ ID NO:6:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Tyr  Ala  Asp  Ala  Ile  Phe  Thr  Asn  Ser  Tyr  Arg  Lys  Val  Leu  Gly  Gln
1                   5                        10                       15

Leu  Ser  Ala  Arg  Lys  Leu  Leu  Gln  Asp  Ile  Xaa  Ser
                    20                   25
```